(12) United States Patent
Benevides

(10) Patent No.: US 7,238,937 B2
(45) Date of Patent: Jul. 3, 2007

(54) SUBSTRATE ADAPTER FOR USE IN MASS SPECTROSCOPY ANALYSIS

(75) Inventor: Christopher Benevides, Tiverton, RI (US)

(73) Assignee: Waters Investments LimitedDE (US)

( * ) Notice: Subject to any disclaimer, the term of this patent is extended or adjusted under 35 U.S.C. 154(b) by 0 days.

(21) Appl. No.: 11/471,168

(22) Filed: Jun. 19, 2006

(65) Prior Publication Data

US 2007/0023682 A1 Feb. 1, 2007

Related U.S. Application Data

(63) Continuation of application No. PCT/US2005/000492, filed on Jan. 7, 2005.

(60) Provisional application No. 60/536,043, filed on Jan. 13, 2004.

(51) Int. Cl.
*H01L 21/31* (2006.01)

(52) U.S. Cl. .................. 250/288; 435/6; 435/287.2; 435/7.1

(58) Field of Classification Search ............ None
See application file for complete search history.

(56) References Cited

U.S. PATENT DOCUMENTS

| 2002/0110902 A1 | 8/2002 | Prosser et al. |
| 2003/0073324 A1 | 4/2003 | Matijasevic et al. |
| 2006/0252047 A1* | 11/2006 | Ekstrom et al. ............... 435/6 |

* cited by examiner

*Primary Examiner*—Nikita Wells
*Assistant Examiner*—Zia R. Hashmi
(74) *Attorney, Agent, or Firm*—Anthony J. Janiuk

(57) ABSTRACT

Disclosed herein is a device for holding a substrate having one or more samples in a position for ionizing the samples with a light energy source. The device has a receiving plate with a receiving surface, a back surface and an edge defining an outline. One or more receiving lips project from the receiving surface. The receiving surface receives the back face of the substrate with at least one edge received by the receiving lips for positioning the substrate for ionization of the sample. The device also has at least one substrate clip that has a front finger and a back finger for capturing and aligning the substrate. The front finger extends across the thickness of the receiving plate and substrate to engage the front edge of the substrate to hold the substrate in position. The back finger engages the back surface of the receiving plate. The receiving plate cooperates with the space in a matrix assisted laser desorption ionization mass spectrometer to hold the samples in position for ionization.

50 Claims, 6 Drawing Sheets

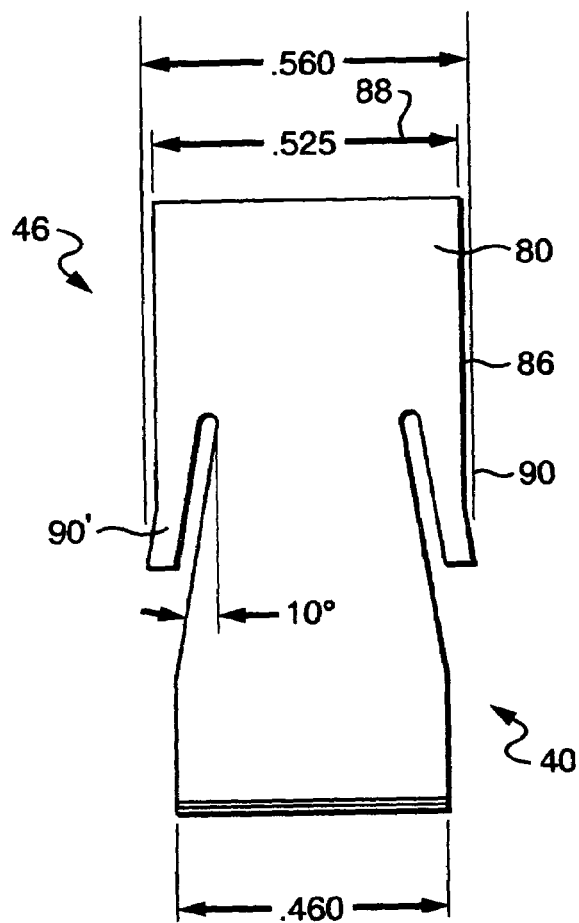
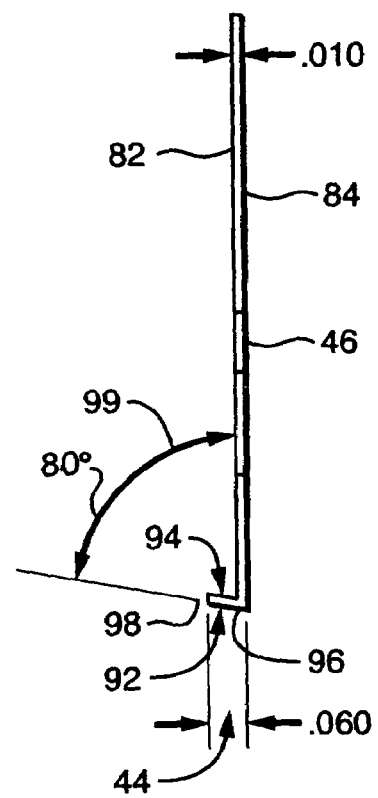
FIG. 4A
FIG. 4B

SUBSTRATE ADAPTER FOR USE IN MASS SPECTROSCOPY ANALYSIS

CROSS REFERENCE TO RELATED APPLICATIONS

This application claims priority from U.S. Provisional patent Application No. 60/536,043, filed Jan. 13, 2004 and PCT Application PCT/US2005/000492, filed Jan. 7, 2005. The contents of these applications are incorporated herein by reference.

STATEMENT ON FEDERALLY SPONSORED RESEARCH

N/A

FIELD OF THE INVENTION

The field of the subject invention is mass spectrometry and more particularly the invention pertains to providing a means for holding a substrate for mass spectrometry during desorption and ionization of an analyte.

BACKGROUND OF THE INVENTION

Mass spectrometry is used to measure the mass of a sample molecule, as well as the mass of the fragments of a sample molecule to identify that sample. The simplest mass spectrometers introduce a gaseous, electrically neutral sample into a vacuum, normally at pressures of 10−6 torr or less. Silverstein, et al, Spectrometric Identification of Organic Compounds, p. 7 (John Wiley & Sons, Inc. 1963). The sample then passes through an electron beam.

The fast-moving electrons from the electron beam strike electrons on the sample being studied, ejecting one or more electrons from the sample. After a subject sample molecule has lost an electron, the sample has a net positive charge, or is "ionized."

Mass spectrometry measures the ratio of the mass of the molecule to the ion's electric charge. The mass is customarily expressed in terms of atomic mass units, called Daltons. The charge or ionization is customarily expressed in terms of multiples of elementary charge. The ratio of the two is expressed as a m/z ratio value (mass/charge or mass/ionization ratio). Because the ion usually has a single charge, the m/z ratio is usually the mass of the ion, or its molecular weight (abbreviated MW). Often, the terms m/z, the mass of the sample in Daltons (or molecular weight, abbreviated MW) are used interchangeably.

Molecules that are not easily rendered gaseous are more difficult to study with mass spectrometry. Accordingly, many modern advances in mass spectroscopy address problems regarding the handling of liquid or solid samples. When a molecule is 'on' a substrate, the sample is adsorbed to that substrate. Desorption is the process by which a molecule adsorbed on a substrate is removed from the substrate. Removing a molecule from a surface is "desorbing" a molecule from that surface. When desorbed, the molecule may be "vaporized", that is rendered into a gaseous state. Instead of starting with a gaseous sample, as basic mass spectrometry does, desorption mass spectrometry starts with the sample adsorbed on a substrate and desorbs the sample, thereby providing the gaseous sample to the mass spectrometer.

A desorption mass spectrometric methodology used for analysis of biological samples is matrix assisted laser desorption/ionization mass spectrometry (MALDI-MS). In conventional MALDI, the sample is typically dissolved into a solid, ultraviolet-absorbing, crystalline organic acid matrix. The liquid matrix/sample is deposited onto a inert base plate in a specific pattern and allowed to dry into target spots. Pulsed laser radiation ionizes some sample molecules while vaporizing the spot carrying the sample with the vaporized matrix. Many MALDI instruments are preconfigured to ionize the spots in sequence to maximize throughput of the system.

MALDI-MS allows for desorption and ionization of non-volatile samples (e.g., biological samples) from a solid-state phase directly into the gas phase without charring, fragmentation, or chemical degradation. MALDI-MS is used to analyze substances such as polypeptides, polynucleotides, proteins, DNA fragments, biopolymers, and other large molecules. The development of proton transfer ionization has made biomolecular mass spectroscopy possible.

MALDI is severely limited in the study of small molecules. The MALDI matrix interferes with measurements below a m/z of approximately 700, called the low-mass region, which varies somewhat depending on the matrix used. Even with large molecules, MALDI has significant limitations. The matrix and matrix fragments can form adducts with the sample ion that can cause the measured signal to have a range of molecular weights. A spectrum from such an analysis may have substantially shortened peak heights.

New methods of desorbing samples have been developed that utilize a substrate to hold the sample rather than having the sample be mixed with a matrix and then be adsorbed to the base plate as was previous practice with MALDI spectrometers. Substrates of porous silicon have been used with laser equipped mass spectrometers to perform analyses of samples. As used herein, the term "DIOS" refers to desorption ionization on silicon, a structure that is described in U.S. Pat. No. 5,882,496 the contents of which is hereby expressly incorporated herein by reference in its entirety. A DIOS substrate (referred to as a chip) typically has dimensions of approximately three to five centimeters and a thickness of 0.5 millimeters. The sample, generally in the form of an aqueous solution in which one or more compounds are dissolved, is received on the porous silicon surface of the substrate. When used in the determination of mass and charge information of ions formed by laser ionization, the substrate is placed in close proximity to the inlet of a mass spectrometer. The laser is discharged or pulsed, ionizing and vaporizing a portion of the sample but leaving the substrate behind. The vapor, ions and gases are drawn into the inlet of the mass spectrometers for analysis.

The DIOS methodology provides the beneficial effects of having a direct laser desorption/ionization technique for use in biomolecular and other analyses. The DIOS methodology addresses the unfulfilled needs of the present methods for dramatically simplified sample preparation. Sample preparation is simplified because of the absence of the matrix or the need for covalent linkage of the analyte to the substrate. Further, substrates do not need to be tailored to the needs of a particular sample, and the DIOS method has a tolerance for salts and buffers.

In order to utilize the DIOS chip with existing MALDI instruments, ways need to be developed to secure the substrates in the instruments without introducing chemicals. It would be preferable to have the chips positioned repeatably so that the instrument does not need to be retargetted between chips. Further, when the analysis of the samples on the substrate is complete, an easy way to remove and dispose of used substrate would be useful. The present invention addresses these needs.

SUMMARY OF THE INVENTION

The present invention is directed to a device for holding one or more substrates for use in an instrument. In particular, each substrate can have one or more samples arranged in a pattern of positions for being ionized by a light energy source associated with a matrix assisted laser desorption/ionization mass spectrometer. Each substrate has a front face providing a working surface for receiving one or more samples, a back face, at least one edge and a thickness.

The device is comprised of a receiving plate and at least one substrate clip. The receiving plate has a back surface, a thickness, at least one edge defining an outline and at least one receiving surface. Each receiving surface is for receiving the back face of a substrate. Each receiving surface has one or more receiving lips projecting from the receiving surface for receiving at least one edge of the substrate.

Each substrate clip has at least one front finger and at least one back finger. The front finger has a width and a length sufficient to extend beyond the thickness of the substrate lying on the receiving plate when being utilized. The back finger extends from the front finger to assume a position on the back surface of the receiving plate.

When being used, the receiving plate receives the one or more substrates. Each substrate is on one of the plurality of receiving surfaces with some edges abutting one or more receiving lips to orient the substrate in position for ionization of one of the samples by the light energy source. Each substrate is engaged by at least one substrate clip at the front edge of the substrate. The substrate clip further engages the back surface of the receiving plate to capture the substrate in position.

In one embodiment, each receiving surface has at least one edge formed of a portion of the edge of the receiving plate. In a preferred embodiment, the device has one receiving surface for receiving one substrate. The receiving plate is conductive and further it may be metallic. In one embodiment, the substrate is a semiconductor. The semiconductor may be silicon or germanium. With a conductive receiving plate and a semiconductor substrate, an electrical connection is made between the substrate and the receiving plate.

In one embodiment, the device is constructed and arranged to cooperate in the space of one or more metallic plates for use in matrix assisted laser desorption/ionization mass spectrometers. Preferably, the substrate is a desorption/ionization on silicon (DIOS) chip. The desorption/ionization on silicon chip has porous semiconductor regions arranged in a pattern that conforms to the targets of the matrix assisted laser desorption ionization mass spectrometer.

In one embodiment, the receiving plate has at least one indent in the outline. This indent provides an area where the front finger can contact the front face of the substrate while the substrate clip remains within a projection of the outline across the indent. The substrate clip holds the substrate by exerting a compressive force on the substrate between the front finger and the receiving lips. To accomplish this, at least one receiving lip has a substrate contacting surface. The substrate contacting surface is planar and forms an angle with the receiving surface. The angle is equal to or less than 90°, preferably between 75° and 85°. The receiving lips extend above the receiving surface for a distance equal to about twice the thickness of the substrate.

In one embodiment, the receiving plate has at least one recess in the back surface. Each recess has a width, a base surface and at least one sidewall. The recesses are for receiving the back finger of the substrate clip. The sidewall defines a sidewall plane and the base surface defines a base plane. The intersection of the base plane and sidewall plane defines an angle. This angle is preferably between 40° and 50°. In one embodiment, the recess intersects with the edge of the receiving plate. Preferably, the recess slidingly engages the back finger.

Preferably, the receiving plate has at least one indent in the outline that is centered on the recess. The indent provides an area where the front finger can contact the front face of the substrate while the substrate clip remains within a projection of the outline across the indent. The indent centered on the recess has a width that is equal to or greater than the width of the recess. This embodiment facilitates insertion of the substrate clip on the receiving plate.

The substrate clip is formed of a resilient material. In one embodiment, the substrate clip is formed of a metallic material and an electrical connection can be made between the substrate clip and the substrate. In one embodiment, the back finger of the substrate clip comprises a planar member having a first face, a second face, at least one edge, a width and a tensioning means for holding the substrate clip in the recess. When the back finger is received by the recess with the first face against the base surface of the recess, the second face is recessed below the back surface of the receiving plate. In one embodiment, the back finger has at least one spring element for engaging the at least one sidewall. The spring element projects from the edge of the back finger. In one embodiment, the back finger has two spring elements for engaging the sidewall.

In one embodiment of the device, the front finger comprises a planar blade having a first face, a second face and a tip. The first face forms an angle with the back finger. The angle is preferably between 75° and 85°. With this angle, the first face of the front finger presses the substrate to the receiving surface when the clip engages the front edge of the substrate. In addition, the front finger may have a thickening at the tip for further engaging the front surface of the substrate.

In one embodiment, the receiving plate has a rectangular shape having four edges. A first edge is opposite a third edge and a second edge is opposite a fourth edge. The second and fourth edges are at right angles to the first and third edges. The embodiment has the one or more receiving lips arranged with at least one first receiving lip disposed along the first edge of the receiving surface and at least one second receiving lip disposed along the second edge of the receiving surface. The first receiving lip has a substrate contacting surface. The substrate contacting surface is planar and forms an angle that is equal to or less than 90° with the receiving surface. Preferably, the angle is between 75° and 85°. In one embodiment, the receiving plate has at least one indent in either the third edge or the fourth edge for providing an area where the front finger can contact the front face of the substrate while the substrate clip remains within a projection of the edge across the indent.

The device is used in a method of holding at least one substrate having one or more samples in a pattern of positions for ionizing the samples with a light energy source. The substrate has a front face for receiving one or more samples, a back face and a thickness. The back face has one or more back edges which define a length and width along the back face. The front face has one or more front edges which define a length and width along the front face.

The method comprises providing a device having a receiving plate and at least one substrate clip. The receiving plate has a back surface, a thickness, at least one edge defining an outline and at least one receiving surface. The receiving surface is for receiving the back face of the substrate. The receiving surface has one or more receiving lips projecting from the receiving surface for receiving at least one edge of the substrate. Each substrate clip has at least one front finger and at least one back finger. The front finger has a width and a length sufficient to extend beyond the thickness of the substrate lying on the receiving plate when being utilized. The back finger extends from the front finger to assume a position on the back surface of the receiving plate.

The method then involves placing the substrate on the receiving surface. The substrate is placed with at least one front edge abutting one or more receiving lips. This orients the substrate in position for ionization of a sample by a light energy source.

An edge of the front face of the substrate is then engaged by the at least one substrate clip to hold the substrate in the position. Finally, the device with the substrate is placed in the space of one or more metallic plates for use in a matrix assisted laser desorption ionization mass spectrometer.

Preferably, the back surface of the receiving plate has at least one recess for receiving the back finger of the substrate clip. Then, the method further comprises slidingly engaging the back finger in the at least one recess.

Other systems, methods, features and advantages of the present invention will be or become apparent to one skilled in the art upon examination of the following drawings and detailed description. It is intended that all such additional systems, methods, features and advantages be included within this description, be within the scope of the present invention, and be protected by the accompanying claims.

DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numbers designate corresponding parts throughout the several views. The above noted and other features of the invention are illustrated in the accompanying drawings, in which:

FIG. 4A is a top view of an embodiment of a substrate clip;

FIG. 4B is a side view of the substrate clip of FIG. 4B; and

DETAILED DESCRIPTION

The present invention is directed to a device for holding one or more substrates for use in an instrument. A preferred instrument is a matrix-assisted laser desorption/ionization (MALDI) mass spectrometer. The device is used when the samples to be desorbed and ionized are directly deposited on a substrate rather than being mixed with a matrix and deposited on the base plate previously used by MALDI spectrometers. Each substrate can have one or more locations for holding samples. These locations are arranged in the pattern that the MALDI instrument uses for ionizing a sequence of samples by a light energy source. Using this mechanism, the substrate can be used in MALDI instruments that sequence through a predefined sequence of target locations. When using the device, the substrates(s) are captured and aligned without the use of adhesives, thereby simplifying the preparation and maintaining the vacuum of the mass spectrometer.

Figure 1A:
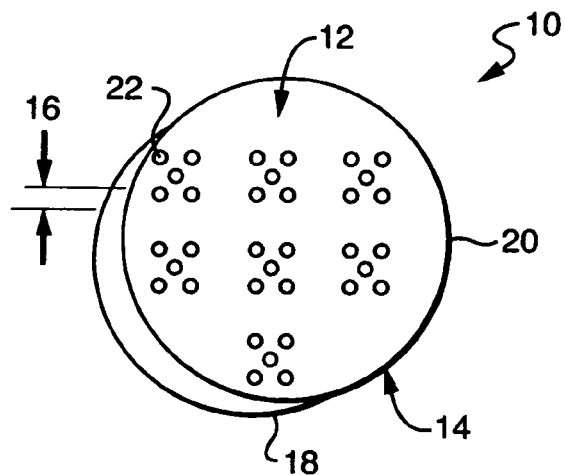
FIG. 1A is a perspective view of a circular substrate.
Figure 1B:
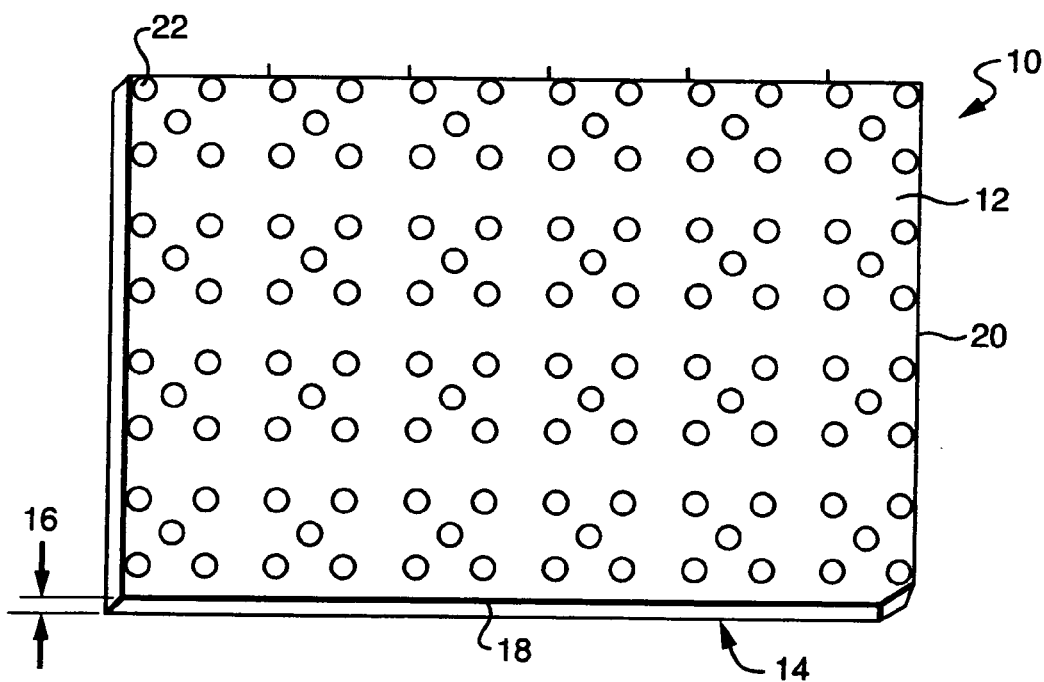
FIG. 1B is a perspective view of a rectangular substrate.

FIGS. 1A and 1B illustrates substrates. Each substrate 10 has a front face 12 for receiving one or more samples 22, a back face 14 and a thickness 16. The back face 14 has one or more back edges 18, which define a length and width along the back face 14. The front face 12 has one or more front edges 20, which define a length and width along the front face 12. The samples 22 are preferably placed on the front face 12 in patterns that conform to the patterns used by the analyzing instrument. FIG. 1 illustrates a round substrate having a diameter of between 1 in to 4 in (2.54 to 10.16 cm). A rectangular substrate has dimensions of between 2–5.25 in (5.08–13.34 cm) long by 1–3.5 in (2.54–8.89 cm) wide. FIG. 1B illustrates a preferred rectangular substrate having dimensions of approximately 2 in by 1.45 in (5.08 cm×3.68 cm). Substrates are typically between 400–700 µm thick.

Figure 2A:
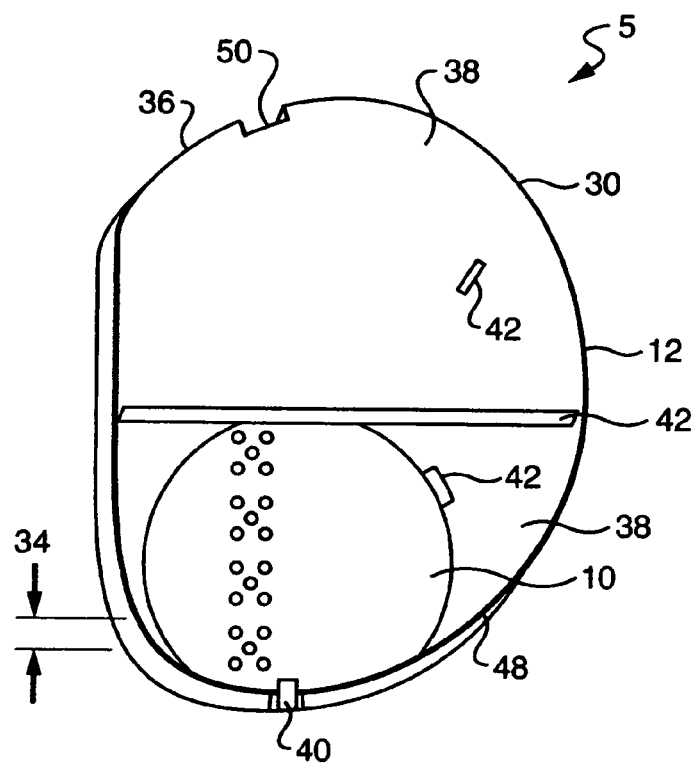
FIG. 2A is a top view of an embodiment of the receiving plate.
Figure 2B:
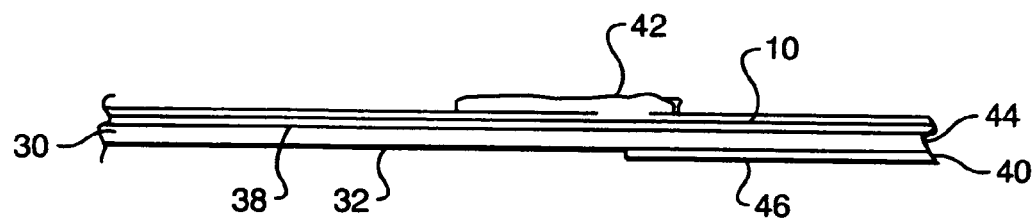
FIG. 2B is a side view of the receiving plate of FIG. 2A.
Figure 3A:
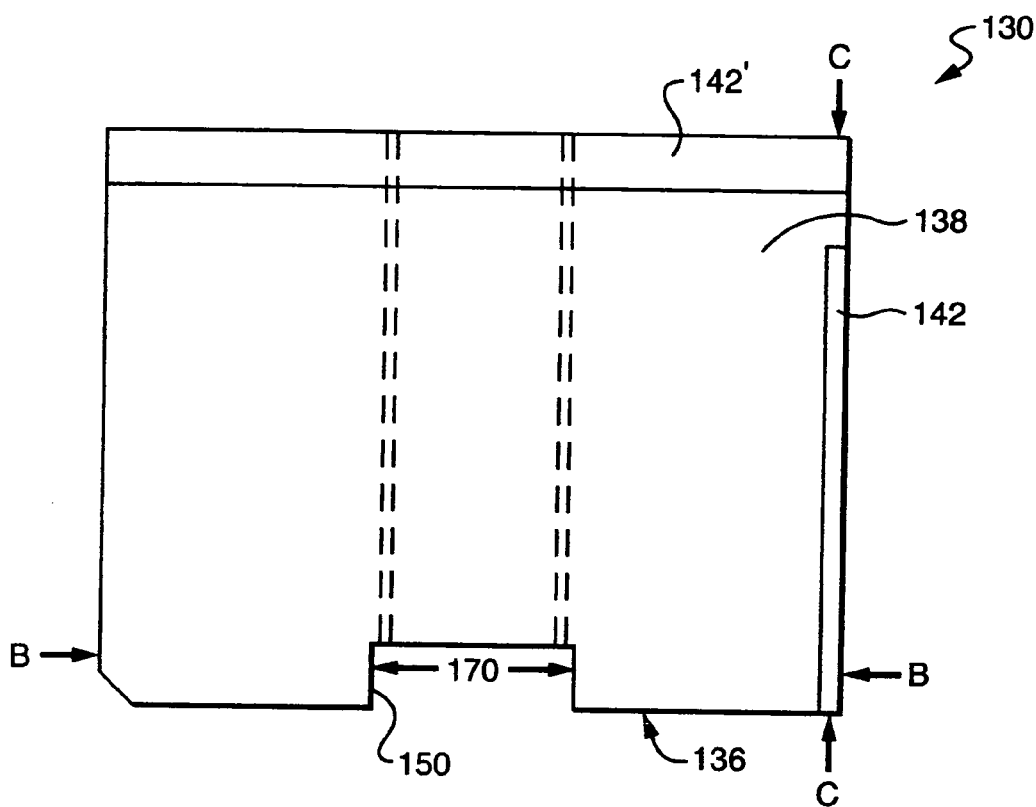
FIG. 3A is a top view of an embodiment of a receiving plate.
Figure 3B:
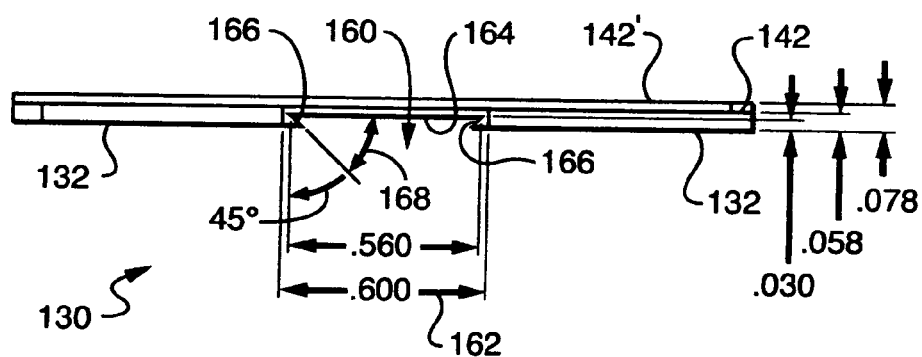
FIG. 3B is a side view of the embodiment of FIG. 3A along line b—b.
Figure 3C:
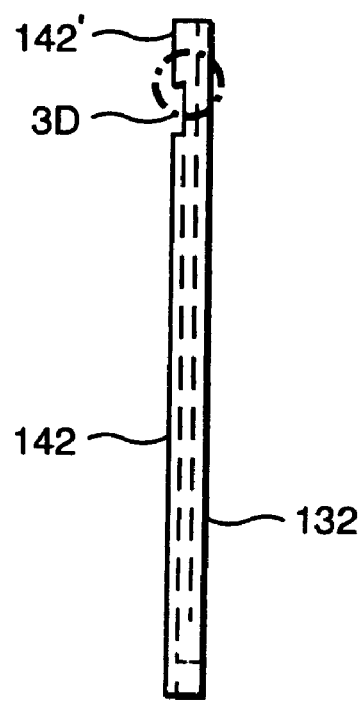
FIG. 3C is a side view of the receiving plate of FIG. 3A along line c—c.
Figure 3D:
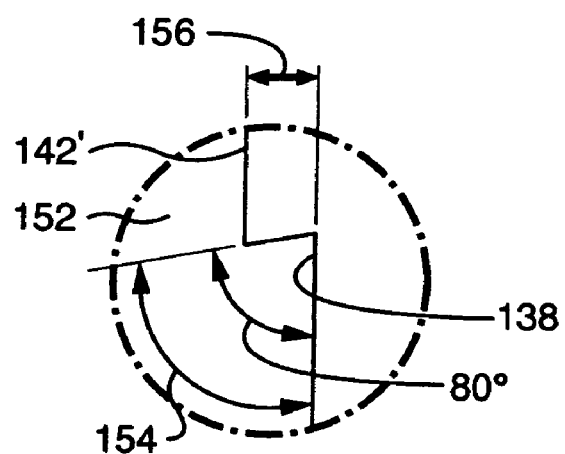
FIG. 3D is a detail of FIG. 3C.

The device 5, as shown in FIGS. 2A and 2B is comprised of a receiving plate 30 and at least one substrate clip 40. The receiving plate 30 has a back surface 32, a thickness 34, at least one edge 36 defining an outline and at least one receiving surface 38. Each receiving surface 38 is for receiving the back face 14 of a substrate 10. Each receiving surface 38 has one or more receiving lips 42 projecting from the receiving surface 38 for receiving at least one edge 18, 20 of the substrate 10.

Each substrate clip 40 has at least one front finger 44 and at least one back finger 46. The front finger 44 has a width and a length sufficient to extend beyond the thickness of the substrate 10 lying on the receiving surface 38 when being utilized. The back finger 46 extends from the front finger 44 to assume a position on the back surface 32 of the receiving plate 30.

When being used, the receiving plate 30 receives the one or more substrates 10. Each substrate 10 is on one of the plurality of receiving surfaces 38 with some edges 18, 20 abutting one or more receiving lips 42 to align the substrate 10 in position for the ionization of one of the samples by the light energy source. Each substrate 10 is engaged by at least one substrate clip 40 at the front edge 20 of the substrate 10. The substrate clip 40 further engages the back surface 32 of the receiving plate 30 to hold the substrate 10 in position. At least one indent 50 may be cut into the edge 36 to allow substrate clip 40 to be installed and remain within the outline of the receiving plate. Those skilled in the art will readily recognize that the outline may take several forms with the indent 50 cut into an edge formed by a straight edge or an arc of a curve.

As illustrated, each receiving surface 38 has at least one edge 48 formed of a portion of the edge 36 of the receiving plate 30. In a preferred embodiment, the device 10 has one receiving surface 38 for receiving one substrate 10. The receiving plate 30 may be conductive and further it may be metallic. The metallic receiving plate 30 may also be magnetic to further conform to the characteristics of conventional base plates. Preferably, the substrate 10 is a semiconductor. The semiconductor may be silicon or germanium. With a conductive receiving plate 30 and a semiconductor substrate 10, an electrical connection can be made between the substrate 10 and the receiving plate 30.

As illustrated, the device 5 is constructed and arranged to cooperate in the space of one or more metallic plates for use in matrix assisted laser desorption ionization mass spectrometers. In this embodiment, the device 5 with the substrate clip 40 holding the substrate 10 to the receiving plate 30 fits in the space normally utilized by the base plate. The device 5 and substrate 10 are so arranged that the when the device 5 is placed in the space, the front face 12 of the substrate 10 is a flat plane allowing the laser to focus on each of the targets 22. The device 5 may be used with a substrate 10 significantly smaller than the receiving surface 38 as long as the receiving lips 42 are arranged to place an edge of the substrate 10 close to an edge 36 of the receiving plate 30 to be engaged by the substrate clip 40. In one embodiment, the substrate 10 is a desorption/ionization on silicon (DIOS) chip. The desorption/ionization on silicon chip has porous semiconductor regions, made by the process described in U.S. Pat. No. 6,004,450 and incorporated herein by reference its entirety, arranged in a pattern of targets of the matrix assisted laser desorption ionization mass spectrometer. When the device holding the DIOS chip is installed in place of the base plate of a MALDI instrument, the targets of the DIOS chip are aligned within 0.5 to 0.1 mm which is sufficiently precise for the laser to vaporize the samples held on the targets.

As illustrated in FIGS. 3A–3D the receiving plate may have an outline that is rectangular forming an essentially rectangular receiving plate 130. The receiving plate is slightly larger than the substrate it holds. For a rectangular substrate having dimensions of 2 in×1.45 in, the receiving plate would be approximately 2.165 in×1.614 in (5.5 cm×4.1 cm). The illustrated receiving plate is approximately 0.06±0.005 in thick with receiving surfaces extending approximately 0.02±0.005 in above the receiving surface. The receiving plate 130 has one indent 150 in the outline. This indent 150 is deep enough to extend under the substrate and provides an area where the front finger 44 can contact the front face 12 of the substrate 10 while the substrate clip 40 remains within a projection of the outline across the indent 150. The substrate clip 40 holds the substrate (not shown) by exerting a compressive force on the substrate between the front finger 44 and the one or more receiving lips 142. To accomplish this, at least one receiving lip 142' has a substrate contacting surface 152. The substrate contacting surface 152 is planar and forms an angle 154 with the receiving surface 138. The angle 154 is equal to or less than 90°, preferably between 75° and 85°. This angle 154 provides sufficient overhang that, when a substrate is in compressive contact with the substrate contacting surface 152, the substrate is held to the receiving surface 138 by the angled contacting surface 152. The receiving lips 142 extend above the receiving surface 138 for a distance equal to about twice the thickness of the substrate.

As illustrated, the receiving plate 130 has one recess 160 upon the back surface 132. The recess 160 has a width 162, a base surface 164 and at least one sidewall 166. The recess 160 is for receiving the back finger 46 of the substrate clip 40. The width is sufficient to receive the back finger 46 and compress a tensioning device. The sidewall 166 defines a sidewall plane. The base surface is cut into the body of the receiving plate 130 to about one half its depth. In the figure, the recess is 0.030±0.005 in deep. The recessed base surface 164 defines a base plane. The intersection of the base plane and sidewall plane defines an angle 168. The angle 168 is between 40° and 50°. The recess 160 intersects with an edge 136 of the receiving plate 130 and slidingly engages the back finger 46.

The receiving plate 130 has one indent 150 in the outline that is centered on the recess 160. The indent 150 provides an area where the front finger 44 can contact the front face 12 of the substrate 10 while the substrate clip 40 remains within a projection of the outline across the indent 150. The indent 150 centered on the recess 160 has a width 170 that is equal to or greater than the width 162 of the recess. This arrangement facilitates insertion of the substrate clip 40 on the receiving plate 130. Those skilled in the art will recognize that the dimensions illustrated above are applicable to one instrument. However, the arrangement of receiving surface, indent and recess is applicable to alternate sizes and outlines formed of straight edges or arcs of curves.

The substrate clip 40 is formed of a resilient material. In one embodiment, the substrate clip 40 is formed of a metallic material and an electrical connection is made between the substrate clip 40 and the substrate 10. As illustrated in FIGS. 4A and 4B, the back finger 46 of the substrate clip 40 comprises a planar member 80 having a first face 82, a second face 84, at least one edge 86, a width 88 and a tensioning means 90 for holding the substrate clip 40 in the recess 160. The substrate clip 40 has a thickness approximately one-third to one-half the thickness of the recess 162. In the illustration, the finger 40 is 0.01±0.003 in thick. When the back finger 46 is received by the recess 160 with the first face 82 disposed against the base surface 164 of the recess 160, the second face 84 is recessed below the back surface 132 of the receiving plate 130. Therefore, the substrate clip 40 does not interfere with the engagement of the back surface 132 when the device 105 is installed. In one embodiment, the back finger 46 has at least one spring element 90' for engaging the at least one sidewall 166. The spring element 90' projects from the edge 80 of the back finger 46. In a preferred embodiment, the back finger 46 has two spring elements 90, 90' for engaging the sidewall 166.

The front finger 44 comprises a planar blade 92 having a first face 94, a second face 96 and a tip 98. The first face 94 forms an angle 99 with the back finger 46. The angle 99 is preferably between 75° and 85°. With this angle, the first face 84 of the front finger 44 presses the substrate 10 to the receiving surface 138 when the clip 40 engages the front edge 14 of the substrate 10. In addition, the front finger 44 may have a thickening (not shown) at the tip 99 for further engaging the front surface 12 of the substrate 10.

Figure 5:
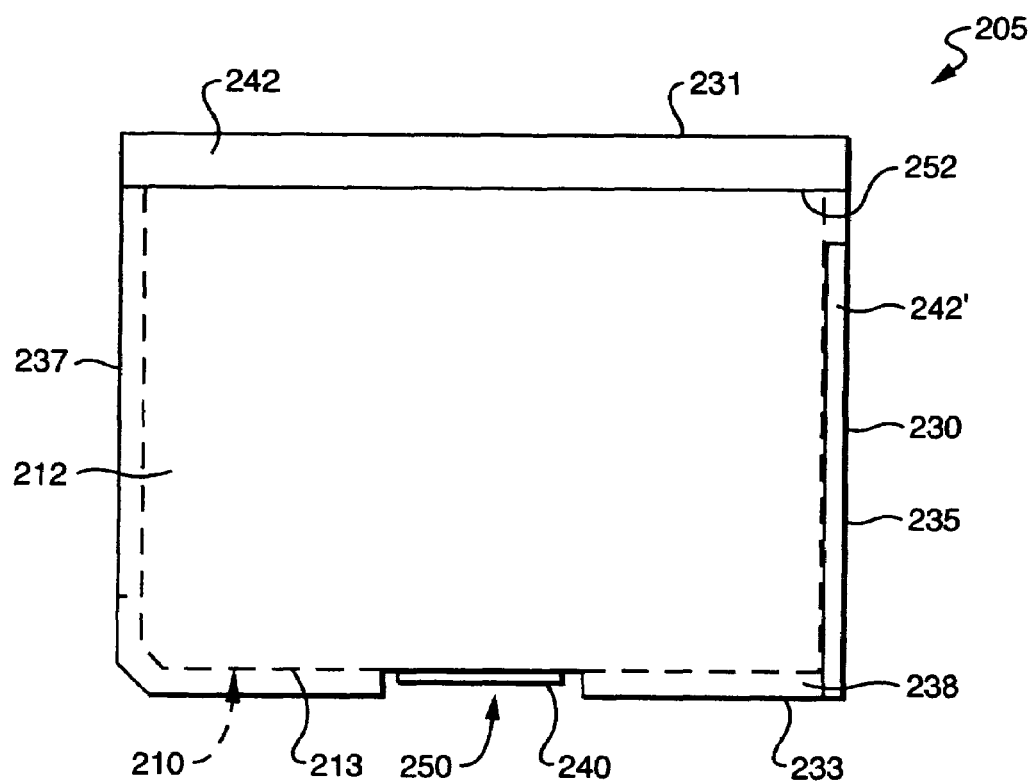
FIG. 5 is a top view of an embodiment of the device holding a substrate.

Turning now to FIG. 5, the receiving plate 230 has a rectangular shape having four edges and is adapted for receiving a rectangular substrate 210. A first edge 231 is opposite a third edge 233 and a second edge 235 is opposite a fourth edge 237. The second and fourth edges 235, 237 are at right angles to the first and third edges 231, 233. The embodiment has the one or more receiving lips 242, 242' arranged with at least one first receiving lip 242 disposed along the first edge 231 of the receiving surface 238 and at least one second receiving lip 242' disposed along the second edge 235 of the receiving surface 238. The first receiving lip 242 has a substrate contacting surface 252. The substrate contacting surface 252 is planar and forms an angle that is equal to or less than 90° with the receiving surface 238. In one embodiment the angle is between 75° and 85°. The first receiving lip 242 therefore provides an overhang against which the substrate 210 may be pushed and prevented from breaking contact with the substrate contacting surface 252. The receiving plate 230 has at least one indent 250 in either the third edge 233 or the fourth edge 237. The indent 250 provides an area where the front finger 244 can contact the front face 212 of the substrate 210 while the substrate clip 240 remains within a projection of the edge across the indent 250. As shown in FIG. 5, the substrate 210 is supported by the receiving surface 238. One edge of the substrate 210 is contacting the substrate contacting surface 252 and so is under the overhang on the first receiving lip 242. A second edge is aligned with the second receiving lip 242' to position the substrate. The substrate 210 spans the indent 250. The figure shows substrate clip 240 inserted in the recess (not shown) and contacting the outer edge 213 of the substrate 210. The substrate clip is both pushing the substrate 210 into contact with the substrate contacting surface 252 and pressing the substrate 210 against the receiving surface 238.

The device 205 is used in a method for holding a substrate 210 having one or more samples (not shown) on a working surface in a pattern of positions to facilitate the ionizing of the samples with a light energy source. The samples are on the front face 212 of the substrate 210. The substrate has a back face and a thickness. The back face has one or more back edges which define a length and width along the back face. The front face 212 has one or more front edges that define a length and width along the front face 212.

The method comprises providing the device 205 having a receiving plate 230 and at least one substrate clip 240. The receiving plate 230 has a back surface, a thickness, at least one edge defining an outline and at least one receiving surface 238. The receiving surface 238 is for receiving the back face of a substrate 210. The receiving surface 238 has one or more receiving lips 242 projecting from the receiving surface 238 for receiving at least one edge of the substrate 210. Each substrate clip 240 has at least one front finger and at least one back finger. The front finger has a width and a length sufficient to extend just beyond the thickness of the substrate 210 lying on the receiving plate 230 when being utilized. The back finger extends from the front finger to assume a position on the back surface of the receiving plate 230.

The method then involves placing the substrate 210 on the receiving surface 238. The substrate 210 is placed with at least one front edge abutting one or more receiving lips 242. This orients the substrate 210 in position for ionization of a sample by a light energy source. An edge 213 of the front face 212 of the substrate 210 is then engaged by at least one substrate clip 240 to hold the substrate 210 against at least one receiving lip 242 and against the receiving surface 238. Finally, the device 205 with the substrate 210 is placed in the space of one or more metallic plates for use in a matrix assisted laser desorption ionization mass spectrometer.

In a preferred method, the back surface of the receiving plate 230 has at least one recess for receiving the back finger of the substrate clip 240. Then, the method further comprises slidingly engaging the back finger in the at least one recess.

While a rectangular shape has been used to represent the receiving plate in the figures, it will be recognized that alternate shapes can be utilized. The figures illustrate a receiving plate having flat surfaces for the back surface and the receiving surface. The back surface of the receiving plate may have an alternate contour to match the surface of the enclosing space. Similarly, the receiving surface may have a contour that complements the back face of the substrate. The combination of contours of the enclosing space, receiving plate surfaces and back face of the substrate result in the front face of the substrate being flat and directed at the laser source.

EXAMPLES

Those skilled in the art will recognize, or be able to ascertain using no more than routine experimentation, numerous equivalents to the specific procedures, embodiments, claims and examples described herein. Such equivalents were considered to be within the scope of this invention and covered by the claims appended hereto. The contents of all references, issued patents, and published patent applications cited throughout this application are hereby incorporated by reference. The advantages of the inventive device will be illustrated by the following example.

A substrate holder conforming generally to the structure illustrated in FIG. 5 was constructed for a DIOS chip. Sample was placed on the porous spots of the chip and allowed to dry. The chip was slid onto the receiving surface and placed in contact with the two receiving lips. The substrate clip was installed with the back finger inserted into the recess until the front finger contacted the edge of the substrate. The assembly could now be handled by the edges of the receiving plate. When the assembly was held approximately level, the chip was not displaced. The assembly could be oriented with either the edges of the receiving plate with receiving lips or the edge of the receiving plate with the substrate clip down without displacing the chip. If the assembly were held with the edge of the receiving plate that had neither a receiving lip nor a substrate clip contacting the chip, the chip could be displaced from the receiving surface if sufficient force were exerted. The assembly was ready to be inserted in the MALDI instrument within 2 seconds. There was no need to use special equipment or special handling procedures. When the device was assembled in suitably clean conditions, no additional cleaning step was required after the chip was secured.

The substrate holder was immediately ready to be reused after all tests were performed on one DIOS chip. Withdrawing the substrate clip frees the substrate from the clean receiving surface. It can now be disposed of and a new DIOS chip installed. The inventive device provides consistency in positioning the substrates in the target cavity of the MALDI mass spectrometer. No retargeting of the spectrometer is required between substrates. One skilled in the art will appreciate further features and advantages of the invention based on the above-described embodiments. Accordingly, the invention is not to be limited by what has been particularly shown and described, except as indicated by the appended claims.

The invention claimed is:

1. A device for holding one or more substrates each said substrate having one or more samples in a position for ionizing said samples with a light energy source, each said substrate having a front face for receiving one or more samples and a back face, said back face having one or more back edges which define a length and width along said back face, said front face having one or more front edges which define a length and width along said front face and each said substrate having a thickness, said device comprising:

a receiving plate, said receiving plate having a back surface, a thickness, at least one edge defining an outline and at least one receiving surface, each said receiving surface for receiving said back face of a substrate and each said receiving surface having one or more receiving lips projecting from each said receiving surface for receiving at least one edge of said substrate; and at least one substrate clip, each said substrate clip having at least one front finger and at least one back finger, said front finger having a width and a length to extend beyond said thickness of said substrate and said receiving plate and said back finger extending from said front finger to assume a position on said back surface of said receiving plate;

wherein said receiving plate receives said one or more substrates, each said substrate on one of said plurality of receiving surfaces and abutting said one or more receiving lips for aligning said substrate in position for ionization of a sample by said light energy source and each said substrate is engaged by at least one substrate clip at said front edge of said substrate, said at least one substrate clip further engaging said back surface of said receiving plate for holding said substrate in said position.

2. The device of claim 1 wherein each said receiving surface has at least one edge formed of a portion of said at least one edge of said receiving plate.

3. The device of claim 2 wherein said device has one said receiving surface for receiving one said substrate.

4. The device of claim 1 wherein said receiving plate is conductive.

5. The device of claim 4 wherein said receiving plate is metallic.

6. The device of claim 1 wherein said substrate is a semiconductor.

7. The device of claim 6 wherein said substrate is silicon or germanium.

8. The device of claim 4 wherein an electrical connection is made between said substrate and said receiving plate.

9. The device of claim 1 wherein said receiving plate is constructed and arranged to cooperate in the space of one or more metallic plates for use in matrix assisted laser desorption ionization mass spectrometers.

10. The device of claim 9 wherein said substrate is a desorption/ionization-on-silicon chip.

11. The device of claim 10 wherein said desorption/ionization-on-silicon chip has porous semiconductor regions arranged in a pattern of targets of said matrix assisted laser desorption ionization mass spectrometer.

12. The device of claim 1 wherein said receiving plate has at least one indent in said outline for providing an area wherein said front finger can contact said front face of said substrate while said substrate clip remains within a projection of said outline across said indent.

13. The device of claim 1 wherein said substrate clip holds said substrate by exerting a compressive force on said substrate between said front finger and said one or more receiving lips.

14. The device of claim 1 wherein at least one receiving lip has a substrate contacting surface, said substrate contacting surface is planar and said substrate contacting surface forms an angle with said receiving surface.

15. The device of claim 14 wherein said angle is equal to or less than 90°.

16. The device of claim 15 wherein said angle is between 75° and 85°.

17. The device of claim 1 wherein said receiving lips extend above said receiving surface for a distance equal to about twice said thickness of said substrate.

18. The device of claim 1 wherein said receiving plate has at least one recess upon said back surface, said at least one recess having a width, a base surface and at least one sidewall, said at least one recess for receiving said back finger of said at least one substrate clip.

19. The device of claim 18 wherein said at least one sidewall defines a sidewall plane and said base surface defines a base plane which base plane and sidewall plane define an angle.

20. The device of claim 19 where said angle is between 40° and 50°.

21. The device of claim 18 wherein said at least one recess slidingly engages said back finger.

22. The device of claim 18 wherein said at least one recess intersects with said at least one edge of said receiving plate.

23. The device of claim 22 wherein said receiving plate has at least one indent in said outline for providing an area wherein said front finger can contact said front face of said substrate while said substrate clip remains within a projection of said outline across said indent and said indent is centered on said recess and has a width that is equal to or greater than said width of said recess.

24. The device of claim 13 wherein said substrate clip is formed of a resilient material.

25. The device of claim 24 wherein said substrate clip is formed of a metallic material and an electrical connection is made between said substrate clip and said substrate.

26. The device of claim 18 wherein said back finger of said substrate clip comprises a planar member having a first face, a second face, at least one edge, a width and a tensioning means for holding said substrate clip in said recess.

27. The device of claim 26 wherein, when said back finger is received by said recess with said first face disposed against said base surface of said recess, said second face is recessed below said back surface of said receiving plate.

28. The device of claim 26 wherein back finger has at least one spring element for engaging said at least one sidewall.

29. The device of claims 28 wherein said spring element projects from said edge of said back finger.

30. The device of claim 29 wherein said back finger has two spring elements for engaging said sidewall.

31. The device of claim 24 wherein said front finger comprises a planar blade having a first face, a second face and a tip, said first face forming an angle with said back finger.

32. The device of claim 31 wherein said angle is between 75° and 85°.

33. The device of claim 31 wherein said first face of said front finger presses said substrate to said receiving surface when said clip engages said front edge of said substrate.

34. The device of claim 31 wherein said front finger has a thickening at said tip for engaging said front surface of said substrate.

35. The device of claim 9 wherein said receiving plate has a rectangular shape having four edges, a first edge opposite a third edge and a second edge opposite a fourth edge, said second and fourth edges at right angles to said first and third edges.

36. The device of claim 35 wherein said one or more receiving lips comprises:

at least one first receiving lip disposed along said first edge of said receiving surface; and at least one second receiving lip disposed along said second edge of said receiving surface.

37. The device of claim 36 wherein said first receiving lip has a substrate contacting surface, said substrate contacting surface is planar and said contacting surface forms an angle with said receiving surface.

38. The device of claim 37 wherein said angle is equal to or less than 90°.

39. The device of claim 33 wherein said angle is between 75° and 85°.

40. The device of claim 35 wherein said receiving plate has at least one indent in an edge selected from said third edge and said fourth edge for providing an area wherein said front finger can contact said front face of said substrate while said substrate clip remains within a projection of said edge across said indent.

41. A method of holding a substrate having one or more samples in a position for ionizing said samples with a light energy source, said substrate having a front face for receiving one or more samples, and a back face, said back face having one or more back edges which define a length and width along said back face and said front face having one or more front edges which define a length and width along said front face, and said substrate having a thickness, said method comprising:
  providing a receiving plate, said receiving plate having a back surface, a thickness, at least one edge defining an outline and at least one receiving surface, each said receiving surface for receiving said back face of a substrate and each said receiving surface having one or more receiving lips projecting from said receiving surface for receiving at least one edge of said substrate; and
  providing at least one substrate clip, each substrate clip having at least one front finger and at least one back finger, said front finger having a width and a length to extend beyond the thickness of said substrate and said receiving plate and said back finger extending from said front finger to assume a position on said back surface of said receiving plate;
  placing said substrate on of said receiving surfaces with at least one front edge abutting one or more receiving lips for aligning said substrate in position for ionization of a sample by a light energy source; and
  engaging an edge of said front face of said substrate and said back surface of said receiving plate with said at least one substrate clip to hold said substrate in said position.

42. The method of claim 41 wherein said receiving plate is constructed and arranged to cooperate in the space of one or more metallic plates for use in a matrix assisted laser desorption ionization mass spectrometer and the method further comprises placing said device in the space of one or more metallic plates for use in said matrix assisted laser desorption ionization mass spectrometer.

43. The method of claim 41 wherein said receiving plate is conductive.

44. The method of claims 41 wherein said substrate is a semiconductor.

45. The method of claim 41 wherein said receiving plate has at least one indent in said outline for providing an area wherein said front finger can contact said front face of said substrate while said substrate clip remains within a projection of said outline across said indent.

46. The method of claim 41 wherein said back surface of said receiving plate has at least one recess for receiving said back finger of said substrate clip, said method further comprising slidingly engaging said back finger in said at least one recess.

47. The method of claim 41 wherein said substrate clip is formed of a metallic material and an electrical connection is made between said substrate clip and said substrate.

48. The method of claim 47 wherein said back finger of said substrate clip comprises a planar member having a first face, a second face, at least one edge, a width and a tensioning means for holding said substrate clip in said recess.

49. The method of claim 48 further comprising receiving said back finger in said recess with said first face disposed against said base surface of said recess whereby said second face is recessed below said back surface of said receiving plate.

50. A method of holding one or more substrates each said substrate having one or more samples in a position for ionizing said samples with a light energy source, each said substrate having a front face for receiving one or more samples, and a back face, said back face having one or more back edges which define a length and width along said back face and said front face having one or more front edges which define a length and width along said front face, and said substrate having a thickness, said method comprising:
  providing a receiving plate, said receiving plate having a back surface, a thickness, at least one edge defining an outline and at least one receiving surface, each said receiving surface for receiving said back face of a substrate and each said receiving surface having one or more receiving lips projecting from each said receiving surface for receiving at least one edge of said substrate;
  providing at least one substrate clip, each substrate clip having at least one front finger and at least one back finger, said front finger having a width and a length to extend beyond the thickness of said substrate and said receiving plate and said back finger extending from said front finger to assume a position on said back surface of said receiving plate;
  placing each said substrate on one of said receiving surfaces with at least one front edge abutting said one or more receiving lips for aligning said substrate in position for ionization of a sample by a light energy source; and
  engaging an edge of said front face of each said substrate and said back surface of said receiving plate with said at least one substrate clip to hold said substrate in said position.

* * * * *